United States Patent [19]

Ono

[11] 4,112,073

[45] Sep. 5, 1978

[54] MEDICINAL COMPOSITION COMPRISING ADRENAL CORTICAL HORMONE AND THYROID STIMULATING HORMONE RELEASING HORMONE

[75] Inventor: Hiroomi Ono, Chofu, Japan

[73] Assignee: Takeda Chemical Industries, Ltd., Osaka, Japan

[21] Appl. No.: 721,547

[22] Filed: Sep. 8, 1976

[30] Foreign Application Priority Data

Sep. 9, 1975 [JP] Japan .................................. 50-109777
Mar. 15, 1976 [JP] Japan .................................. 51-28290

[51] Int. Cl.$^2$ ..................... A61K 37/00; C07C 103/52
[52] U.S. Cl. ........................... 424/177; 260/112.5 TR
[58] Field of Search ............... 424/177, 240, 179, 113, 424/243, 112.5 TR

[56] References Cited

U.S. PATENT DOCUMENTS 3,503,951  3/1970  Iselin et al. ........................... 424/179

OTHER PUBLICATIONS

Lafille et al., Chem. Abstracts, vol. 77, 1972, parag. 42985v.

*Primary Examiner*—Natalie Trousof
*Assistant Examiner*—Cary Owens
*Attorney, Agent, or Firm*—Wenderoth, Lind & Ponack

[57] ABSTRACT

A medicinal composition comprising both adrenal cortical hormone and thyroid stimulating hormone releasing hormone has such excellent properties as increasing the therapeutic effects and suppressing side effects of the adrenal cortical hormone.

14 Claims, No Drawings

MEDICINAL COMPOSITION COMPRISING ADRENAL CORTICAL HORMONE AND THYROID STIMULATING HORMONE RELEASING HORMONE

The present invention relates to a medicinal composition comprising both adrenal cortical hormone (hereinafter referred to as ACH) and thyroid stimulating hormone releasing hormone (hereinafter referred to as TSH-releasing hormone).

Heretofore, ACH has been administered to mammals for various purposes, e.g. to make use of the antiexudative, antipruritic, antiallergic, antiinflammatory, carbohydrate-metabolism promoting, immunosuppressive and other activities of such hormones. However, a large variety of diseases are too intractable to be completely cured by ACH. Among such diseases are diarrhea and pneumonia in young animals of the weaning age, the onsets of which are said to be occasioned by various stresses and improper breeding conditions, chronic diarrhea in adult animals, pruritic chronic skin diseases such as eczema, external and internal otitels which are chronic exudative diseases, and pustular interdigital pyrodermatitis.

Moreover, if used in an improper manner or in an unsuitable dose, and, for that matter, even when used at a normal dose level, ACH causes such troubles as a decline in milk production [Journal of the American Veterinary Medical Association, Vol. 157, No. 7, pp. 941–946; Journal of Dairy Science, Vol. 56, No. 7, pp. 896–902]. This has posed problems in the application of such a hormone to mammals. For example, significant declines in milk production are observed even when medicinally acceptable doses of ACH are applied to domestic animals (e.g. dairy cows and goats) with mastitis, ketosis, arthritis, dermatitis, endometritis, vaginitis, allergic diseases or inability to stand before and after parturition and it is for this reason that the use of ACH is substantially restricted. It has, therefore, been a desideratum to have a procedure developed to arrest the decline of milk production which would otherwise be caused by the application of ACH for the cure of diseases.

The intensive research undertaken to establish a medicine capable of curing such diseases and suppressing such side effects led the present inventor to a surprising discovery that, by dosing a mammal with TSH-releasing hormone in conjunction with ACH, there can be obtained an outstanding therapeutic effect which cannot be obtained by the administration of ACH alone, and the side effects of ACH can be suppressed. The above finding was followed by further research which has culminated in the completion of this invention.

Thus, the first object of this invention is to provide a medicinal composition comprising both ACH and TSH-releasing hormone, which has such excellent properties as increasing a therapeutic effect and suppressing a side effect of ACH. The second object is to provide a method for producing the medicinal composition by incorporating ACH and TSH-releasing hormone in a single dosage form. The third object is to provide a method for increasing a therapeutic effect and suppressing a side effect of ACH by administering TSH-releasing hormone in conjunction with ACH. Other objects will be made clear from the description and claims hereinafter.

The ACH employable according to this invention may be natural or synthetic, thus being exemplified by 9α-fluorocortisone, 9α-fluorocortisol, prednisone, prednisolone, triamcinolone (9α-fluoro-16α-hydroxyprednisolone), medrol (6α-methylprednisolone), dexamethasone (9α-fluoro-16α-methylprednisolone), betamethasone (9α-fluoro-16α-methylprednisolone), paramethasone (6α-fluoro-16α-methylprednisolone), flumethasone (6α, 9α-difluoro-16α-methylprednisolone) and so forth. Among them, dexamethasone, betamethasone and flumethasone are conveniently employed. These hormones may be employed in the form of physiologically acceptable esters, such as phosphates, acetates, nicotinates, etc. or physiologically acceptable salts such as alkali metal salts, e.g. sodium, potassium and lithium salts, and alkaline earth metal salts, e.g. calcium salts.

The TSH-releasing hormone is commonly exemplified by L-pyroglutamyl-L-histidyl-L-prolinamide (thyrotrophin releasing hormone; TRH) and compounds having TRH-like activity, such as L-2-oxooxazolidine-4-carbonyl-L-histidyl-L-prolinamide, L-trans-5-methyl-2-oxooxazolidine-4-carbonyl-L-histidyl-L-prolinamide, L-2-oxothiazolidine-4-carbonyl-L-histidyl-L-prolinamide (German Patent Application No. P 2408324.7 laid open to public inspection on Aug. 29, 1974 as OLS No. 2408324) and so forth. These hormones may also be employed in the form of physiologically acceptable salts such as the acid addition salts of inorganic acids (e.g. hydrochloric acid, etc.) and of organic acids (acetic acid, tartaric acid, etc.).

The aforementioned drug containing both ACH and TSH-releasing hormone may be prepared in optional dosage forms such as injections (intramuscular, subcutaneous, intravenous, etc.), oral preparations (powders, tablets, capsules, pills, etc.), topical preparations (ointments, liquids, sprays, aerosols, etc.), infusions and implants (intrauterine, intramamary, etc.) and so forth by per se known procedures. Although advantageous among them are injections and topical preparations, the former is more frequently employed in this field of the art.

The relative amounts of ACH and TSH-releasing hormones may be determined according to the particular dosage form, the disease to be treated and other factors. Generally speaking, the ratio is about 1 (dexamethasone equivalent): 0.05 to 5, advantageously 0.05 to 2, and especially 0.1 to 1. The preferred ratio in each dosage form is; in the case of injections, about 1 (dexamethasone equivalent): 0.05 to 1, advantageously 0.1 to 1; in the case of oral preparations, about 1 (dexamethasone equivalent): 1 to 5, advantageously 1 to 2; and in the case of topical preparations, infusions and implants, about 1 (dexamethasone equivalent): 0.5 to 5, advantageously 0.5 to 2. The 'dexamethasone equivalent' is an index number representing the relative clinical effect of any ACH with the effect of dexamethasone being taken as unity. The equivalent values for some typical ACH are given below.

| ACH | Clinical effect[1] | Equivalent |
| --- | --- | --- |
| Dexamethasone | 30.0 | 1 |
| Hydrocortisone | 1.0 | 30 |
| Prednisolone | 4.0 | 7.5 |
| Prednisone | 4.0 | 7.5 |
| Methylprednisolone | 5.0 | 6 |
| Triamcinolone | 5.0 | 6 |
| Paramethasone | 10.0 | 3 |
| Betamethasone | 30 | 1 |
| Flumethasone | 150 | 0.2 |

[1]: "Adverse Reactions to Drugs" p.217(1975), published by Takeda Chemical Industries, Ltd., Japan.

It will thus be clear that, according to this invention, betamethasone, as used in lieu of dexamethasone, may be used in the same proportion as dexamethasone but, where use is made, for instance, of triamcinolone, the clinical efficacy of which is one-sixth of that of dexamethasone, the preferred compounding ratios are; in the case of injections, about 6 (triamcinolone): about 0.05 to 1 (thyrotrophin releasing hormone); in the case of oral preparations, about 6: 1 to 5; and in the case of topical preparations, infusions and implants, about 6: 0.5 to 5.

In the manufacture of the medicinal composition according to this invention, use may be made of a suitable carrier or vehicle, if necessary. As examples of such carrier or vehicle, various materials that will not interfere with the activities of the medicaments may be mentioned. Thus, excipients, binders, lubricants, colorants, flavorants, odoriferants, suspending agents, solubilizers and so forth may be incorporated. In addition to such vehicles, the medicinal composition of this invention may further contain various kinds of medicines for supplementing the effect of the medicinal composition of the present invention or for expecting concomitantly exhibiting other medicinal effects. As such medicines, there may, for example, be vitamins such as pantothenic acid, nicotinic acid, vitamin $B_1$, vitamin $B_2$, vitamin $B_6$, vitamin $B_{12}$, vitamin C, vitamin D, biotin, folic acid, vitamin K, vitamin E, vitamin P, inositol, orotic acid, lipoic acid, etc.; compounds having vitamin-like activities (e.g. the corresponding derivatives, salts, etc.); antimicrobial agents such as tetracycline, chlortetracycline, oxytetracycline, chloramphenicol, neomycin, dextromycin, kanamycin, trichomycin, mikamycin, penicillin, ampicillin, sulfoxacillin, cephalosporin, sulfaisomidine, sulfioxazole, sulfadimethoxine, sulfachloropyridazine, sulfamethazine, sulfaisazole, sulfamethoxypyridazine, etc., including their salts and other derivatives; streptomycins such as dihydrostreptomycin, streptothricin, streptomycin, etc.; macrolide antibiotics such as oleandomycin, leucomycin, tylosin, erythromycin, spiramycin, lincomycin, pikromycin and so forth.

When used against the various diseases in mammals for which ACH have heretofore been indicated, the medicinal composition of this invention accomplishes satisfactory therapeutic effects which cannot be obtained by the application of ACH alone. Particularly, in such cases as exhudative diseases (e.g. external otitis, internal otitis, interdigital pyodermatitis, etc.), pruritic diseases (e.g. eczema, chronic eczema, etc.), allergic diseases (e.g. diarrhea in young animals in or near the weaning stage, chronic diarrhea in adult animals, etc.), inflammatory diseases (e.g. pneumonia, bronchitis, etc.) and so forth, the composition accomplishes outstanding therapeutic effects of the order which cannot be obtained by conventional chemotherapy. As aforementioned, the medicinal composition of this invention is characterized by its eminent therapeutic effects. In addition, the present drug offers another advantage that the presence of TSH-releasing hormone therein suppresses the physiological functional disorders that would otherwise be caused by the sole use of ACH. For example, when a pharmaceutically effective dose of ACH is given to animals (dairy cows, goats, etc.), a marked decline in milk production takes place, thus imposing a substantial limitation on the application of ACH. However, the medicinal composition of this invention does not cause such declines in milk production by virtue of the TSH-releasing hormone it contains.

The dosage of the medicinal composition of this invention is determined according to the subject mammal, the purpose of administration, the route of administration and other factors. Normally, the composition is preferably administered at such a dose that the dosage level of the ACH contained in the composition will be the same as its dosage level ordinarily used when said hormone is used alone. It is also generally preferable to see to it that the titer of ACH will be 0.1 to 200 mg per dose. More particularly, for large animals such as cattle and horses, the preferred dose is 50 to 200 mg of prednisolone, 10 to 30 mg of dexamethasone, 2 to 5 mg of flumethasone, 6 to 30 mg of triamcinolone or 10 to 30 mg of betamethasone. For intermediate animals such as pigs and sheep, the preferred dose is 10 to 50 mg of prednisolone, 0.5 to 10 mg of dexamethasone, 0.2 to 1 mg of flumethasone, or 2 to 10 mg of triamcinolone or betamethasone. For small animals such as dogs and cats, it is desirable to give 1 to 20 mg of prednisolone, 0.2 to 2 mg of dexamethasone, 0.2 to 0.5 mg of flumethasone, 1 to 3 mg of triamcinolone or 0.5 to 3 mg of betamethasone, to name but a few examples. Generally, the medicinal composition of this invention is applied once daily, normally for one to several days. If necessary, it may be given over an extended period of time at a frequency of once to twice weekly.

The following examples are intended to describe this invention in further detail and should by no means be construed as limiting the scope of the invention.

EXAMPLE 1

Some examples of the medicinal composition according to this invention are prepared as follows:

| A. Injection | |
|---|---|
| (1) sodium dexamethasone phosphate | 20 mg. |
| (2) TRH | 2 mg. |
| (3) phenol | 100 mg. |
| (4) sodium metabisulfite | 16 mg. |
| (5) NaCl | 180 mg. |

All ingredients are dissolved in distilled water to make 20.0 ml of the solution (pH 6.5–7.5). The solution is suitably separated and filled into ampoules. The atmosphere in the ampoules is replaced with nitrogen gas. All the processes are conducted under sterile conditions.

| B. Hydrophilic ointment | |
|---|---|
| (1) dexamethasone | 0.1 g. |
| (2) TRH tartrate | 0.1 g. |
| (3) propylene glycol | 12.0 g. |
| (4) cetyl alcohol | 25.0 g. |
| (5) white petrolatum | 25.0 g. |
| (6) polyoxyethylene stearyl ether | 5.0 g. |
| (7) methyl p-hydroxybenzoate | 0.025 g. |
| (8) propyl p-hydroxybenzoate | 0.015 g. |
| (9) distilled water | to make a total of 100 g. |

A mixture of (4), (5) and (6) is heated to 75° C to make Mixture I. On the other hand, ingredients of (1), (7) and (8) are dissolved in (3) under heating (Mixture II), and (2) is dissolved in (9) under heating (Mixture III). Mixture III is added to Mixture II and the mixture is maintained at a temperature of 78° C (Mixture IV). Mixture IV is added to Mixture I with stirring, and the resultant emulsion is cooled to solidify.

| C. Tablet | |
|---|---|
| (1) dexamethasone | 0.5 mg. |
| (2) TRH | 1.0 mg. |
| (3) lactose | 64.0 mg. |
| (4) corn starch | 34.0 mg. |
| (5) magnesium stearate | 0.5 mg. |
| | 100.0 mg. per tablet |

After mixing (1), (2), (3) and 26 mg. of corn starch thoroughly, the mixture is granulated with paste prepared from 5 mg. of corn starch. The remaining 3 mg. of corn starch and (5) are added to the granules and the mixture is compressed into a tablet of 6.5 mm. in diameter.

EXAMPLE 2

Treatment of eczema (in dogs) with an ointment containing dexamethasone and TRH (1:1).

In view of the fact that ACH ointment (0.1%) has been commonly indicated and used for eczema in dogs, the drug according to this invention was first given to 4 dogs with exudative eczema. First, a hydrophilic ointment containing 0.1% of dexamethasone phosphate was externally applied. As shown below, except that a passing mitigation of inflammation or itchiness was noted in some of the cases, substantially no successful therapeutic result was obtained. Rather, an adverse response, i.e. an increase in the amount of exudate, was in evidence and it was only in a single case that the ointment had a slightly beneficial effect.

| Breed (site of lesion) | Sex | Age | Period of application | Judgement |
|---|---|---|---|---|
| Bulldog (eczema on neck and back) | Male | One year | 5 days | (−) |
| Tosainu (eczema on back and belly) | Male | 2 years | 5 days | (−)* |
| Shibainu (eczema at tail root) | Female | 4 years | 3 days | (−) |
| Spitz (eczema on chest) | Male | 2 years | 5 days | (±) |

*; a passing mitigation of inflammation or itchiness

Then, a hydrophilic ointment containing 0.1% each of dexamethasone phosphate and TRH tartrate was applied to 6 dogs. In all cases, the medication had marked effects as compared with using ACH alone. Thus, the combined use of the two hormones resulted in the onset of response after 2 to 3 days in 5 dogs with exhudative eczema and one dog with exfoliative dermatitis, all the cases being successfully cured with the symptoms disappearing completely or nearly completely by the 3rd or 5th day.

| Breed of dog | Sex | Age | Period of application | Judgement |
|---|---|---|---|---|
| Boxer (neck and root of ear) | Male | 6 months | 3 days | ++ (dried and healed) |
| Maltese (root of tail and inside thigh) | Male | 1 year | 4 days | ++ (dried and healed) |
| Cocker spaniel (belly) | Male | 6 months | 3 days | +++ |
| Shibainu (neck and back) | Female | 3 years | 5 days | ++ |
| Bulldog (eye and forehead) | Female | 2 years | 3 days | +++ |
| *Akitaken (root of tail and belly) | Male | 1 year | 3 days | ++ |

*Exfoliative dermatitis; Applied for 7 days to be on the safe side; Completely cured.
++; very effective
+++; pronouncedly very effective Most of the above cases were treated for eczema. Significant reductions in cure time were obtained in all the cases to which the combined medication was applied and, even in the case with parasitic dermatitis, the redness disappeared with other clinical symptoms being improved.

EXAMPLE 3

Treatment of eczema, external otitis and interdigital pyodermia (all in dogs) with dexamethasone-TRH (4:1 and 16:1) injections.

2.5 ml of a compound injection containing 2 mg of dexamethasone and 125 μg of TRH tartrate was intramuscularly applied to each puppy. A single injection had excellent effects as shown in the following table.

| No. | Breed of dog | Age (years) | Sex | Body weight (kg) | Symptom | Dose per injection | Findings | Judgement |
|---|---|---|---|---|---|---|---|---|
| 1 | Shepherd | 7 (months) | ♂ | 25 | Eczema | 2.5 (ml) | Pruritic eczema with itchiness on proximal parts of thighs. Both the eczema and itchiness disappeared on the day following the medication. | (+++) |
| 2 | Shepherd | 7 (months) | ♀ | 20 | Eczema | 2.5 (ml) | ″ | (+++) |
| 3 | Hybrid | 8 (years) | ♂ | 12 | Chronic eczema | 2.5 (ml) | Systemic eczema with rank odor. Cleansed with Serene ® and repeatedly injected. The lesion started drying up in about 2 weeks. | (+) |

Then, an injection prepared by using 1 mg of dexamethasone and 0.1 mg of TRH per milliliter was instramuscularly given to 3 dogs with eczema and 2 dogs with external otitis. The itchiness disappeared in 2 to 3 days and the rank odor, pus formation and eczema were improved in 5 days. There also was a case in which the red spots disappeared on the next day following the injection. The injection was given three times to each of 2 dogs with chronic eczema. One was injected three times a day and the other was injected twice in a day and once again after a week. Both cases showed marked effects and the latter was completely cured.

| | | | | | |
|---|---|---|---|---|---|
| 1. Hybrid | 12 ♂ 13 | Eczema | 20 ml | Infiltrating eczema at the root of the tail; cleansed with Serene ®. Dried out in a week. | (++) |
| 2. Hybrid | 3 ♂ 17 | Eczema | 20 ml | Corticoid externally applied as adjunct. Complete cure after 3 days. | (++) |
| 4. Doberman | 2 ♂ 31 | Eczema | 30 (ml) | The residue of shampoo at the root of the tail caused the eczema. Cleansed with Serene ®. The itchiness disappeared on the 3rd day. | (++) |
| 5. Maltese | 3.5 ♂ 3.8 | External otitis | 20 | The expulsion of pus was smooth and the odor was eliminated in 3-4 days. The dog became indifferent after a week. | (++) |
| 6. Hybrid | 4 ♂ 17 | Chronic eczema | 20 | Bathing with Muto-Hap ® every day. Three injections eliminated the itchiness. Complete cure after 40 days. | (+) |
| 7. Collie | 6 ♂ 35 | Eczema | 40 | The lesion cleansed. The itchiness was eliminated on the 2nd day. The eczema also disappeared after 3 days. | (++) |
| 8. Pomeranian | 2 ♀ 1.5 | Eczema | 10 | The 5 to 7 red spots around the waist disappeared on the next day following the injection. | (+++) |
| 9. Maltese | 2 ♀ 2.6 | External otitis | 20 | The rank odor, pus and itchiness disappeared around the 5th day. Then, complete cure came after a single cleansing. | (++) |
| 10. Hybrid | 6 ♂ 14 | Chronic eczema | 20 | Dosed for 2 consecutive days, and again after a week. Complete cure after 2 weeks. | (++) |

EXAMPLE 4

Treatment of eczema (in dogs) with a betamethasone-TRH (10:1) compound injection.

2.64 mg/ml of betamethasone, a synthetic ACH which is as potent as dexamethasone, was mixed with 250 μg/ml of TRH to prepare an injection, and two dogs with eczema were intramuscularly treated once. A single injection had a marked effect after 3 to 7 days, resulting in complete or nearly complete cure.

EXAMPLE 5

Treatment of interdigital pyodermia (in dogs) with a dexamethasone-TRH (4:1) compound injection.

This is an intractable skin disease with depth pyodermia which is caused by infection with a Staphylococcus organism. The symptoms include exhudative and pustular lesions.

As in the case of eczema, the conventional remedy consists of injections of an antiinflammatory or/and antiallergic agents at a frequent interval. As an adjunct, injections of an antibiotic to which the causative organism is sensitive has also been indicated. Because of the great depth of the lesion, the disease has been found to be difficult to cure completely and, in not a few cases, the emergence of a resistant strain of organism is responsible for the prolonged course of the disease. In the following case, by culture of the pus-like exhudate collected from the lesion, the causative agent was identified as a kanamycin-resistant strain of Staphylococcus. The course was chronic, accompanied by exhudates and pain at the site, and a surgical treatment was reasonably indicated. However, daily injections of a mixture of 2 mg dexamethasone (2 ml) and 500 μg TRH (2 ml) resulted in a marked mitigation of the redness and swelling of the lesion after 3 days, and the symptoms were substantially absent, with lameness cured, on the 5th day.

A histological examination of the lesion (in the 4th interdigital fold) demonstrated a complete heal. By the end of 3 months, there was a complete cure without a relapse. The age and breed of dog: Bulldog, male, 18 months old. Pyodermia between the 3rd and 4th digits of the right front paw and at the 2nd and 3rd digits of the left front paw.

EXAMPLE 6

Treatment of chronic moist dermatitis (in dogs) with dexamethasone-TRH tartrate (1:2) tablets
Akitaken (dog): 2 years and 6 months old, male, 25 kg
Diagnosis: Chronic moist dermatitis The onset had come at the buttocks and the root of the tail, and had been treated with ACH without success. First, one tablet of 0.5 mg dexamethasone failed to elicit a response. Therefore, on the next day one tablet containing 0.5 mg of dexamethasone and 1 mg of TRH tartrate was orally administered. Because the medication caused the lesion to start drying, another tablet was given on the 3rd day. As an adjunct to the medication, the dog was placed on a controlled regimen. The result was a complete cure.

EXAMPLE 7

Treatment of diarrhea (white diarrhea) in young pigs with a dexamethasone: TRH (10:1) compound injection.

Eight young pigs with body weights in the range of 2.5 to 4 kg, 15 days old [an injection of an antibiotic (1 ml of tylosin, I.M.) on the day immediately preceding the weaning was given for the prophylaxis of respiratory diseases but there was diarrhea on the next day] were intramuscularly dosed with a compound injection containing 1 mg of dexamethasone and 100 μg of TRH per 1.2 ml. In all cases, the feces became normal, with no subsequent abnormalities.

EXAMPLE 8

Treatment of diarrhea in dogs and cats, young and adult, with dexamethasone-TRH (6-1:1) compound injections.

Using mixtures of dexamethasone and TRH in the ratios of 6:1, 2:1 and 1:1, the following 9 dogs, young and adult, and one young and one adult cat, were intramuscularly medicated once. In all cases, a complete cure was obtained.

| Breed | Age | Body weight kg | Dose* ml:ml | Cure confirmed |
|---|---|---|---|---|
| Maltese (male dog) | 8 months | 3 | (6:1) 0.3:0.2 | 10 days(+++) |
| Persian (female cat) | 4 years | 5 | 0.3:0.2 | 10 days(+++) |
| Pomeranian | 3 months | 0.8 | (4:1) 0.1:0.1 | 7 days(+++) |
| (male dog) Dachsund (male dog) | 6 months | 9 | 0.3:0.3 | 14 days(+++) |
| Shibainu (male dog) | 3 months | 2.5 | 0.1:0.1 | 14 days(+++) |
| Maltese (female dog) | 2 months | 1.8 | 0.1:0.1 | 14 days(+++) |
| Siamese (cat) | 6 months | 3 | 0.2:0.2 | 3 days(+++) |
| Kantonken (male dog) | 8 years | 8 | (1:1) 0.2:0.4 | 28 days(+++) |
| Dachshund (male dog) | 4 months | 1.5 | 0.1:0.2 | 21 days(+++) |
| Spitz (hybrid, female dog) | 7 years | 9 | 0.2:0.4 | 21 days(+++) |

*Dexamethasone 1 mg/ml; TRH 0.5 mg/2 ml

EXAMPLE 9

Treatment (antitussive) of bronchitis (in dog) with a dexamethasone-TRH(10:1) compound injection. Hybrid dog, 8 years, 15 kg, laryngobronchitis Appetite normal, body temp. 38.7° C, with severe coughing A compound injection of 2 mg dexamethasone (2 ml) and 0.2 mg TRH(4 ml) caused the coughing to subside on the next day. Then, the dog was further medicated at the same dose. There was a complete cure on the 4th day.

EXAMPLE 10

For each of Group A of animals comprising three healthy dairy cows [average daily milk productions: 17.5 ($A_1$), 15.8 ($A_2$) and 15.5 ($A_3$), kg.] subcutaneously injected with 10 ml of an aqueous solution of 10 mg dexamethasone phosphate, Group B which comprised three healthy dairy cows [average daily productions of milk: 15.5 ($B_1$), 20.5 ($B_2$) and 13.9 ($B_3$) Kg.] injected subcutaneously with 18 ml of an aqueous solution containing 10 mg of dexamethasone phosphate and 2 mg of TRH (tartrate) and Group C [control] comprising three healthy dairy cows [average daily productions of milk: 12.7 ($C_1$), 9.1 ($C_2$) and 11.5 ($C_3$) kg.], the amount of milk secreted during the 8 days following the injection were measured and the variation from the average amount of milk production was determined and expressed in percentage. The values and percents are given in Tables 1, 2 and 3.

Table 1

| | Group A | | | | | |
|---|---|---|---|---|---|---|
| | $A_1$ | | $A_2$ | | $A_3$ | |
| Day of measurement | Milk production (kg) | % | Milk production (kg) | % | Milk production (kg) | % |
| Day of injection | 18.5 | 105.7 | 15.7 | 99.3 | 13.0 | 83.8 |
| 1 day after injection | 12.4 | 70.8 | 12.6 | 79.7 | 10.1 | 65.1 |
| 2 days " | 14.9 | 85.1 | 14.6 | 92.4 | 11.3 | 72.9 |
| 3 days " | 15.5 | 88.5 | 15.0 | 94.9 | 12.6 | 81.2 |
| 4 days " | 17.2 | 98.2 | 15.2 | 96.2 | 12.2 | 78.7 |
| 5 days " | 16.8 | 96.0 | 14.8 | 93.6 | 14.6 | 94.1 |
| 6 days " | 17.0 | 97.1 | 16.3 | 103.1 | 12.8 | 82.5 |
| 7 days" | 17.3 | 98.8 | 15.3 | 96.8 | 13.6 | 87.7 |

Table 2

| Day of measurement | Group B | | | | | |
|---|---|---|---|---|---|---|
| | $B_1$ | | $B_2$ | | $B_3$ | |
| | Milk production (kg) | % | Milk production (kg) | % | Milk production (kg) | % |
| Day of injection | 16.9 | 109.0 | 22.9 | 111.7 | 14.0 | 100.7 |
| 1 day after injection | 14.9 | 96.1 | 18.7 | 91.2 | 13.4 | 96.4 |
| 2 days " | 16.6 | 107.0 | 19.6 | 95.6 | 14.4 | 103.5 |
| 3 days " | 15.6 | 100.6 | 19.9 | 97.0 | 14.0 | 100.7 |
| 4 days " | 14.4 | 92.9 | 20.0 | 97.5 | 13.0 | 93.5 |
| 5 days " | 15.7 | 101.2 | 19.9 | 97.0 | 13.2 | 94.9 |
| 6 days " | 16.6 | 107.0 | 20.8 | 101.4 | 13.2 | 94.9 |
| 7 days " | 15.6 | 100.6 | 19.4 | 94.6 | 13.4 | 96.4 |

Table 3

| Day of measurement | Group C | | | | | |
|---|---|---|---|---|---|---|
| | $C_1$ | | $C_2$ | | $C_3$ | |
| | Milk production (kg) | % | Milk production (kg) | % | Milk production (kg) | % |
| Starting day | 11.7 | 92.1 | 9.5 | 105.5 | 11.5 | 100.0 |
| 1 day after starting day | 13.0 | 102.3 | 9.8 | 108.8 | 11.1 | 96.5 |
| 2 days " | 13.0 | 102.3 | 9.4 | 104.4 | 11.9 | 103.4 |
| 3 days " | 13.2 | 103.9 | 8.9 | 97.8 | 10.7 | 93.0 |
| 4 days " | 12.8 | 100.7 | 9.8 | 107.6 | 10.0 | 86.9 |
| 5 days " | 13.9 | 100.9 | 9.3 | 102.1 | 11.7 | 101.7 |
| 6 days " | 12.0 | 94.4 | 10.0 | 109.8 | 12.5 | 108.6 |
| 7 days " | 13.1 | 103.1 | 8.3 | 91.2 | 12.2 | 106.0 |

It will be seen from Tables 1, 2 and 3 that the declines in milk secretion due to dexamethasone can be definitely arrested by dosing the animals with TRH. The trend of milk production in Group B (dosed according to this invention) was substantially the same as that observed for Group C (control).

EXAMPLE 11

A solution of 10 mg of dexamethasone phosphate in 10 ml of water and a solution of 20 mg of said agent in 20 ml of water were each used to dose animals subcutaneously along with the simultaneous application of 1 mg and 2 mg, respectively, of TRH (in each combination, the weight ratio was 10:1). The amounts of milk produced during one week following the injections were measured and compared with the amounts of milk production during one week before the injections and during the second week following the injections. The results are shown in Table 4.

Table 4

| Dosage | | Milk production (average ± standard deviation) kg | | |
|---|---|---|---|---|
| | | 1 week before injection | 1 week after injection | During 8-14 days after injection |
| Dexamethasone phosphate | 10 mg | 13.09 ± 0.75 | 13.20 ± 0.98 | 11.84 ± 0.81 |
| TRH | 1 mg | | (12.46 ± 0.99)* | |
| Dexamethasone phosphate | 20 mg | 8.43 ± 1.82 | 9.36 ± 1.67 | 8.24 ± 0.65 |
| TRH | 2 mg | | (8.34 ± 1.31)* | |

*: The average milk productions for one week before the injection and during the 8th to 14th days after the injection.

The above experimental data show that, statistically, the milk production of the group dosed with both dexamethasone phosphate and TRH at the same time is not significantly different from the production of milk in the control group.

EXAMPLE 12

A Holstein cow with a body weight of 662 kg was intramuscularly dosed with 10 ml of an aqueous solution of 10 mg betamethasone and 4 ml of an aqueous solution of 1 mg TRH and the amounts of milk produced before and after the injection were measured and compared. The results are set forth in Table 5.

Table 5

| Day of measurement | Milk production, kg | Day of measurement | Milk production, kg |
|---|---|---|---|
| 4 days before injection | 13.9 | 2 days after injection | 12.6 |
| 3 days " | 13.7 | 3 days after injection | 14.6 |
| 2 days " | 14.8 | 4 days after injection | 13.6 |
| 1 day " | 14.2 | 5 days after injection | 12.0 |
| Day of injection | 13.7 | 7 days after injection | 13.2 |
| 1 day after injection | 12.9 | 10 days after injection | 13.7 |

It will be apparent from Table 5 that no decline in milk production occurred when both betamethasone and TRH were injected.

EXAMPLE 13

A Holstein cow weighing 654 kg was intramuscularly dosed with 10 ml of an aqueous solution of 10 mg flumethasone and 4 ml of an aqueous solution of 1 mg TRH, and the amounts of milk produced before and after the injection were measured and compared. The results are set forth in Table 6.

Table 6

| Day of measurement | Milk production, kg | Day of measurement | Milk production, kg |
|---|---|---|---|
| 4 days before injection | 18.5 | 2 days after injection | 14.8 |
| 3 days " | 18.0 | 3 days " | 19.8 |
| 2 days " | 16.5 | 4 days " | 15.4 |
| 1 day " | 14.9 | 5 days " | 13.3 |
| Day of injection | 15.2 | 7 days " | 14.5 |
| 1 day after injection | 14.9 | 10 days " | 15.7 |

It will be apparent from Table 6 that the injection of both flumethasone and TRH prevents a decline in milk production.

EXAMPLE 14

A dairy cow, 3 years old, with chronic mastitis in which the clots (flakes) (++) in milk had persisted even after the application of a synthetic penicillin over the preceding month was intramuscularly administered with a mixed solution of 10 mg of dexamethasone and 1 mg of TRH in distilled water for injections at the frequency of once a day for two consecutive days. This treatment resulted in the disappearance of milk flakes and the cow could thereafter be managed as a healthy animal. Table 7 below shows the amounts of milk production before and after the injection.

Table 7

| Day of measurement | Milk production, kg | Day of measurement | Milk production, kg |
|---|---|---|---|
| 4 days before injection | 8.3 | 1 day after start of injection | 6.0 |
| 3 days " | 8.1 | 2 days " | 5.5 |

Table 7-continued

| Day of measurement | Milk production, kg | Day of measurement | Milk production, kg |
|---|---|---|---|
| 2 days " | 7.6 | 3 days " | 7.8 |
| Starting day of injection | 6.4 | 4 days " | 7.7 |

It will be apparent from Table 7 that the application of TRH in conjunction with the application of dexamethasone cures chronic mastitis without a decline in milk production.

EXAMPLE 15

A dairy cow, 5 years old, with unilateral polycystic follicles was subjected to two follicle disintegrating treatments but could not be cured, with andromaniac symptoms persisting. Therefore, the cow was intramuscularly dosed with a mixed solution of 10 mg dexamethasone and 1 mg of TRH in distilled water for injections. The luteinization of follicles began to be in evidence on the sixth day after the injection and an unmistakable sign of estrus was noted on the 22nd day. Artificial insemination, therefore, was carried out. The amounts of milk produced before and after the injection are shown in Table 8.

Table 8

| Day of measurement | Milk production, kg | Day of measurement | Milk production, kg |
|---|---|---|---|
| 4 day before injection | 17.0 | 1 day after injection | 16.7 |
| 3 days " | 16.8 | 2 days " | 16.5 |
| 2 days " | 17.5 | 3 days " | 16.8 |
| 1 day " | 16.0 | 4 days " | 16.0 |
| Day of injection | 16.5 | 5 days " | 17.2 |

It is apparent from Table 8 that the application of TRH along with dexamethasone leads to a cure of ovarian follicle cyst without affecting the secretion of milk.

EXAMPLE 16

Ketone bodies were found in the milk of a dairy cow towards a peak of milk production. The cow with latent ketosis, therefore, was intramuscularly dosed with a mixed solution of 10 mg of dexamethasone and 1 mg of TRH in 10 ml of distilled water for injections once daily for two consecutive days. The ketone bodies disappeared and the cow went into a peak production phase. The amounts of milk produced before and after the treatment are shown in Table 9.

Table 9

| Day of measurement | Milk production, kg | Day of measurement | Milk production, kg |
|---|---|---|---|
| first injection | 27.0 | 1 day after first injection | 21.0 |
| 2 days " | 25.0 | 2 days " | 20.6 |
| 1 day " | 21.3 | 3 days " | 22.5 |
| Day of first injection | 20.0 | 4 days " | 23.4 |

It will be apparent from Table 9 that the application of TRH along with dexamethasone to cows with latent ketosis leads to a cure of the condition and prevents mastitis without affecting the rate of milk production.

What is claimed is:

1. A medicinal composition for increasing the therapeutic effect of an adrenal cortical hormone which comprises an effective amount of an adrenal cortical hormone selected from the group consisting of 9α-fluorocortisone, 9α-fluorocortisol, prednisone, prednisolone, triamcinolone, medrol, dexamethasone, betamethasone, paramethasone, flumethasone and physiologically acceptable esters and salts thereof, and a thyroid stimulating hormone-releasing hormone selected from the group consisting of L-pyroglutamyl-L-histidyl-L-prolinamide, L-2-oxooxazolidine-4-carbonyl-L-hystidyl-L-prolinamide, L-trans-5-methyl-2-oxooxazolidine-4-carbonyl-L-histidyl-L-prolinamide, L-2-oxothiazolidine-4-carbonyl-L-histidyl-L-prolinamide and physiologically acceptable salts thereof, the ratio of the adrenal cortical hormone to the thyroid stimulating hormone-releasing hormone being about 1 (dexamethasone equivalent): 0.05 to 5 and a acceptable carrier.

2. The medicinal composition according to claim 1, wherein the ratio of said adrenal cortical hormone to said thyroid stimulating hormone-releasing hormone is about 1 (dexamethasone equivalent): 0.05 to 2.

3. A method for increasing the therapeutic effect of an effective amount of adrenal cortical hormone selected from the group consisting of 9α-fluorocortisone, 9α-fluorocortisol, prednisone, prednisolone, triamcinolone, medrol, dexamethasone, betamethasone, paramethasone, flumethasone and physiologically acceptable esters and salts thereof, against exhudative, pruritic, allergic or inflammatory diseases in mammals, or for suppressing the side effect of said adrenal cortical hormone of lessening milk production in animals following administration of said adrenal cortical hormone to said animals, which comprises administering to the patient to be treated a thyroid stimulating hormone-releasing hormone selected from the group consisting of L-pyroglutamyl-L-histidyl-L-prolinamide, L-2-oxooxazolidine-4-carbonyl-L-hystidyl-L-prolinamide, L-trans-5-methyl-2-oxooxazolidine-4-carbonyl-L-histidyl-L-prolinamide, L-2-oxothiazolidine-4-carbonyl-L-histidyl-L-prolinamide and physiologically acceptable salts thereof, in conjunction with the administration of said adrenal cortical hormone to said patient, in a ratio of said thyroid stimulating hormone-releasing hormone to said adrenal cortical hormone of about 0.05 to 5 : 1 (dexamethasone equivalent.)

4. The medicinal composition according to claim 1, wherein said adrenal cortical hormone is in the form of a physiologically acceptable ester or salt.

5. The medicinal composition according to claim 1, wherein said thyroid stimulating hormone-releasing hormone is in the form of a physiologically acceptable salt.

6. The medicinal composition according to claim 1, wherein said adrenal cortical hormone is dexamethasone.

7. The medicinal composition according to claim 1, wherein said adrenal cortical hormone is betamethasone.

8. The medicinal composition according to claim 1, wherein said thyroid stimulating hormone-releasing hormone is L-pyroglutamyl-L-histidyl-L-prolinamide.

9. The method according to claim 3, wherein said adrenal cortical hormone is in the form of a physiologically acceptable ester or salt.

10. The method according to claim 3, wherein said thyroid stimulating hormone-releasing hormone is in the form of a physiologically acceptable salt.

11. The method according to claim 3, wherein said adrenal cortical hormone is dexamethasone.

12. The method according to claim 3, wherein said adrenal cortical hormone is betamethasone.

13. The method according to claim 3, wherein said thyroid stimulating hormone-releasing hormone is L-pyroglutamyl-L-histidyl-L-prolinamide.

14. The method according to claim 3, wherein the ratio of said adrenal cortical hormone to said thyroid stimulating hormone-releasing hormone is about 1 (dexamethasone equivalent) : 0.05 to 2.

* * * * *